Figure 2A:
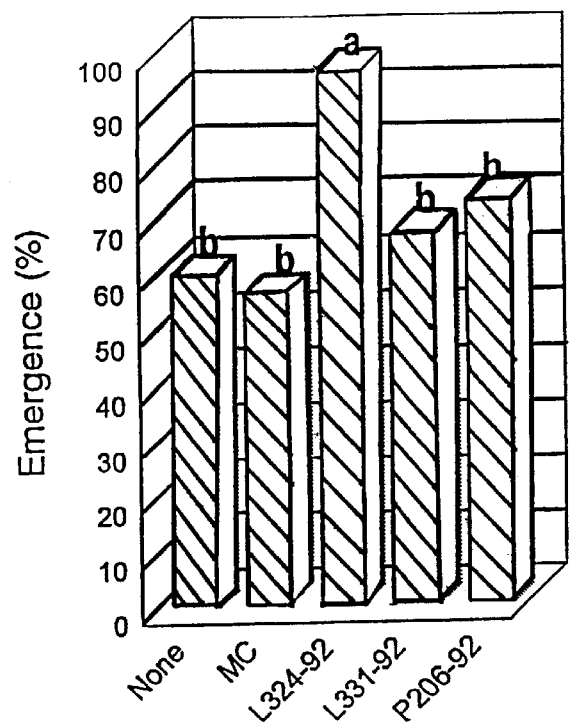

United States Patent [19]
Cook et al.

[11] Patent Number: 5,972,689
[45] Date of Patent: Oct. 26, 1999

[54] **METHODS AND COMPOSITIONS FOR THE SIMULTANEOUS CONTROL OF THE ROOT DISEASES CAUSED BY *GAEUMANNOMYCES GRAMINIS*, RHIZOCTONIA, AND PYTHIUM**

[75] Inventors: R. James Cook; David M. Weller, both of Pullman, Wash.; Dal-Soo Kim, Taejon, Rep. of Korea; Linda S. Thomashow, Pullman, Wash.

[73] Assignees: The United States of America as represented by the Secretary of Agriculture, Washington, D.C.; Washington State University Research Foundation, Pullman, Wash.

[21] Appl. No.: 08/788,604

[22] Filed: Jan. 24, 1997

Related U.S. Application Data

[60] Provisional application No. 60/011,192, Feb. 5, 1996.

[51] Int. Cl.$^6$ .............................. C12N 1/20; A01N 63/00; C12P 1/00; A01C 1/06
[52] U.S. Cl. ........................... 435/252.31; 435/4; 435/41; 435/410; 47/57.6; 424/93.4; 427/4
[58] Field of Search .......................... 47/57.6; 424/93.46; 427/4; 435/252.5, 261, 83, 4, 41, 410, 252.31

[56] References Cited

U.S. PATENT DOCUMENTS

| | | | |
|---|---|---|---|
| 4,456,684 | 6/1984 | Weller et al. | 435/34 |
| 4,647,533 | 3/1987 | Weller et al. | 424/93.47 |
| 5,348,742 | 9/1994 | Howell et al. | 424/93.47 |

OTHER PUBLICATIONS

Kloepper et al. A review of issues related to measuing colonization of plant roots by bacteria. Can. J. Microbiol. vol. 38:1219–1232, Dec. 1992.

Database on BIOSIS, AN 92:123575. A. Renwick, R. Campbell and S. Cos "Assessment of In–Vitro Screening Systems for Potential Biocontrol Agents of *Gaeumannomyces–grainis*," *Plant Pathology* 4D:524–532 (1991) (Abstract).

D.–S. Kim et al., "Biological Control of Three Root Pathogens of Wheat by Bacillus Species," Abstract A663, *Phytopathology*, p. 1406 (Dec. 1993).

D.–S. Kim et al., "Biocontrol Activity of Bacillus sp. Strain 1324 –92 to Root Pathogens of Wheat," Abstract 209, *Phytopathology* 84:1090 (Oct. 1994) handed out Aug. 6 –10, 1994 American Phytopathological Society Annual Meeting.

Annual Research Progress Report, File 60 (CRIS/USDA), Knight–Ridder (1994).

R.J. Cook et al., "Management of Wheat Root Diseases in Reduced –Till Systems", Progress Report for Project No. 2468, to Washington Wheat Commission, Feb. 14, 1996.

S. Nemec et al., "Efficacy of Biocontrol Agents in Planting Mixes to Colonize Plant Roots and Control Root Diseases of Vegetables," Abstract; *Crop Protection* 15:735–742 (Dec. 1996).

D.–S. Kim et al., "Biological Control of Root Diseases of Wheat and Other Crops with Root Associated Bacillus and Transgenic Pseudomonas Species," Dissertation Abstract International 57:3485–3685 (1995).

P. M. Brannen, "Potential Modes of Action for Suppression of Root Diseases and Yield Enhancement When Using *Bacillus subtilis* Seed Inoculants on Cotton," Abstract National Cotton Council, 1:205–208 (Jan. 1995).

R. E. Baird, "Evaluation of Several Pesticides and a Growth Hormone for Control of Pests of Snap Beans," *Fungic. Nematic. Tests*, Abstract 49:92–93 (1994).

*Primary Examiner*—Nancy Degen
*Assistant Examiner*—William Sandals
*Attorney, Agent, or Firm*—M. Howard Silverstein; John D. Fado; Margaret A. Connor

[57] ABSTRACT

Methods and products useful to simultaneously control the root diseases caused by *Gaeumannomyces graminis*, Rhizoctonia, and Pythium in crops susceptible to these root diseases are described. These include a method to identify seed-treatment products for potential to simultaneously control the three kinds of root diseases; Bacillus strains having activity against the three kinds of root diseases and methods of obtaining the same, and compositions comprising a fungicide and a Bacillus strain having activity against the three kinds of root diseases, which compositions are useful for field control of the combination of the three kinds of root diseases.

8 Claims, 4 Drawing Sheets

Planting Wheat in Fields
with a Long History of Wheat

|

Collection of Roots from Seedlings or Stubble

|

Repeated Washing of Root
Fragments in Water (4°C, 30 min, 250 rpm)

|

Heat Treatment
(80°C, 30 min)

|

*In vitro* Screening
for Antifungal Activity (~2000 isolates) against
R. solani AG8, *G. graminis* var. *tritici*, *P. irregulare*

|

Initial Screening
in Growth Chamber (~300 strains)
for Suppression of Rhizoctonia Root Rot

|

Screening in Growth Chamber
(18 strains) for Suppression of
Rhizoctonia Root rot, Take-all and Pythium Root Rot

|

Field Testing at Sites
with History of All Three Pathogens

FIG. 1

*Bacillus* sp. L324-92

*B. subtilis* A13

METHODS AND COMPOSITIONS FOR THE SIMULTANEOUS CONTROL OF THE ROOT DISEASES CAUSED BY *GAEUMANNOMYCES GRAMINIS*, RHIZOCTONIA, AND PYTHIUM

This application claims the benefit of U.S. Provisional Application No. 60/011,192, filed Feb. 5, 1996. The disclosure of said provisional application is incorporated herein by reference.

BACKGROUND OF THE INVENTION

1. Field of the Invention

The present invention relates to methods and compositions useful to simultaneously control root diseases caused by *Gaeumannomyces graminis*, Rhizoctonia, and Pythium species. More particularly, the invention relates to a novel method to identify seed-treatment products for potential to simultaneously control the three kinds of root diseases; microorganism strains having activity against the three kinds of root diseases and methods of obtaining the same; and novel compositions which include a fungicide and biocontrol microorganism, which compositions are useful for field control of the combination of the three kinds of root diseases.

2. Description of the Art

Root diseases caused by *Gaeumannomyces graminis*, Rhizoctonia, and Pythium cause a significant adverse impact on the production of important crops worldwide. The root disease take-all, caused by *Gaeumannomyces graminis* var. *tritici* (Ggt), Rhizoctonia root rot, caused by *Rhizoctonia solani* and *R. oryzae,* and Pythium root rot caused by any of several Pythium species, notably, *Pythium ultimum* and *P. irregulare,* are important root diseases of cereal crops, e.g., wheat, barley, triticale, and rye, worldwide.

Take-all is probably the most important root disease of wheat and related cereals worldwide. This disease is more severe on wheat and triticale than on rye or barley. Among wheats, it tends to be more severe on durum than common wheats. It causes black lesions on both seminal roots (the first roots to emerge from the seed) and the crown roots (secondary roots from the bases of the mainstem and tillers). Take-all also progresses into the crown (tissue where tillers are physically united to the mainstem) and up the tillers and mainstem of infected plants. Plants tend to die as adult but not yet ripened plants, giving a display of white unfilled heads mixed with normal green heads.

Rhizoctonia root rot occurs throughout the United States Pacific Northwest, in Australia, and South Africa, and potentially throughout the temperate regions of the world wherever cereals are grown, especially if grown with reduced or no-tillage (direct drilling). Rhizoctonia root rot caused by *R. solani* AG8 begins as brown cankerous lesions on the seminal and crown roots that eventually girdles and then severs the roots. Plants with roots pruned off by this disease remain stunted and eventually die without making heads. The disease tends to affect plants in patches and has given rise to other names, such as bare patch disease, purple patch, crater disease, and barley stunt disorder. Of all cereals, barley is especially susceptible to *R. solani* AG8. *Rhizoctonia oryzae* infects the embryos of germinating seeds, preventing germination or limiting the formation of seminal roots to only one or two when healthy seedlings produce five or six seminal roots. These two Rhizoctonia species, together with *Rhizoctonia cerealis* and possibly other Rhizoctonia species occur as different mixtures, depending on the soil, cropping systems, weed management practices, and possibly other factors not yet identified.

Pythium is possibly the most widespread soilborne pathogen of cereals in the world, occurring in virtually all agricultural soils. Pythium damage to cereals begins as embryo infections and associated poor emergence or stand establishment and continues as destruction of the fine lateral rootlets and root hairs. Plants with Pythium root rot have the appearance of plants without enough fertilizer, because the disease limits the absorptive capacity of the root system through destruction of fine rootlets and root hairs. There are several species of Pythium with ability to attack cereals, either embryos of germinating seeds, root tips and fine rootlets, or all of these delicate and usually juvenile or meristematic tissues.

The pathogens responsible for take-all and Rhizoctonia root rot survive as hyphae or mycelium in the tissues of host plants colonized through their parasitic activities. Pythium species survive in soil as thick-walled oospores or sporangia produced from nutrients robbed from the plant through parasitism. Usually, all three diseases develop simultaneously on the same plants, although one root disease may dominate.

Although Pythium species are ubiquitous in agricultural soils cropped to cereals, damage to cereals caused by Pythium species, e.g., reduction in seedling emergence and plant vigor, is greatest in soils kept wet, especially if the soils are also naturally high in clay content and with pH values below 6.0. Allowing volunteer cereals (plants that develop from seed spilled or dropped by the harvester on the soil surface) to grow in the field after harvest of one crop until only 1 or 2 days before planting the next crop, then spraying with an herbicide such as glyphosate (ROUND UP, Monsanto), controls the weeds but greatly favors Rhizoctonia root rot. As another example, planting wheat directly into the standing stubble of a previous wheat crop with soil kept moist by sprinkler irrigation or leaving the soil covered with straw favors all three root diseases.

Wheat and other cereals with root disease yield poorly and return less on investments to the grower. Plants with these root diseases also compete poorly with weeds, thereby making it necessary to spend more on herbicides to control weeds. Cereals with root diseases also leave fertilizer unused in the soil, including nitrates, which then may move by leaching below the rooting zone and eventually into ground water. Growers throughout the world continue to use some form of tillage for production of cereals, largely because tillage helps control these root diseases. Tillage causes soils to be more vulnerable to soil erosion. It also requires more energy, and leads to greater evaporation of water needed for yield. Some farmers attempting to use no-till burn the stubble in their fields in the belief that this will provide some relief from root diseases. Stubble burning is both environmentally detrimental and socially unacceptable, especially to people in urban areas and cities that object to having to breathe the smoke produced by stubble burning.

CURRENT PRACTICES AND AVAILABLE TECHNOLOGY

Root diseases of cereals can be controlled by use of crop rotation, that is, by not growing wheat in the same field more than every third or fourth year. However, agriculture like most other enterprises has forced the individual operators to specialize in order to compete. The United States grows some 150 different crops, but less than 15 of these crops (including wheat and barley) occupy more than 90% of U.S. cropland, with the vast majority of farms specialized in the production of a single crop year after year on the same land or two or at most three crops grown in a rotation on any given farm. Because of its importance as a food crop, wheat occupies more land than any other crop grown in the United States, and many wheat farms in areas well-suited to cereals tend to grow wheat every year or at most every other year in the same fields.

Many diseases of wheat, barley, and other crops are controlled by breeding varieties of the crops with resistance to the pathogens. However, this approach has worked mainly for leaf diseases but not for root diseases of wheat, barley, triticale or rye. The only known source of resistance to take-all and Rhizoctonia root rot is in a very distant diploid relative, *Daysapyrum villosum*, but thus far no use has been made of this source of resistance because of the difficulty of transferring genes across such a taxonomically wide distance. No commercial wheat, barley, rye or triticale exists or are under development at the present time in the world with resistance to take-all, Rhizoctonia root rot, or Pythium root rot.

Root diseases of high-value horticultural crops such as strawberries are controlled in the United States by soil fumigation, especially soil fumigation with methyl bromide alone or in mixture with chloropicrin. However, soil fumigation costs more than $1000 per acre and is too expensive for cereals. Moreover, the United States has agreed with other nations to phase out the use of methyl bromide by the year 2001, because it affects the ozone layer. Thus far, no alternative has been discovered that will provide the level of root disease control currently provided by methyl bromide fumigation of the soil.

Seed treatment chemicals provide the only economically affordable chemical option to control root diseases of cereals. However, while seed treatment chemicals may protect the embryos of germinating seeds against infection by Pythium spp. or *R. oryzae*, these chemicals do not protect roots against take-all, Rhizoctonia root rot caused by *R. solani* AG 8, or Pythium spp. This is because the chemicals do not move downward adequately, if at all, into the soil or systemically in the roots from the seed. Even chemicals with systemic action in the plants move upward into the shoots but not downward into roots. Moreover, many seed companies tend not to treat seeds with chemicals because seeds left over after planting cannot be used as feed for livestock or introduced into the food chain and must, therefore, be disposed much as a hazardous waste.

We have conducted extensive tests of commercially available and experimental seed treatment chemicals provided by companies for their potential to control root diseases. These tests have been conducted in wheat fields in cooperation with farmers throughout the Inland Pacific Northwest, including in Idaho, Oregon, and Washington, and dating back to 1982. Similar tests have been conducted with spring barley dating back to 1987. Modest responses of 3–5 bu/A, amounting to 5–10% greater yield have been obtained about one time in five with no response about 80% of the time, where methyl bromide fumigation increased yields by 30–40 bu/A or 50–100%. The large yield response to fumigation but small or no response to seed treatment chemicals shows that root diseases extract an enormous toll on the crop that is not alleviated by the seed treatments.

The best available chemical for control of Pythium, namely metalaxyl, such as sold under the trade name of APRON (Ciba-Geigy Corp., Greensboro, N.C.), has provided yield increases of 5–10% at sites along the Idaho-Washington border where soils have high clay contents, low pH values, and where Pythium is typically the dominant root pathogen. However, yields are increased at these same sites by 25–30% by soil fumigation, showing that the seed treatment falls far short of providing the protection needed for the crop. At other sites, metalaxyl by itself has either given no yield increase, or the yield has decreased due to increased damage from Rhizoctonia root rot, take-all, or both. The chemical does not depress yields of wheat planted into soil with wheat root pathogens virtually eliminated by methyl bromide fumigation; thus, if direct phytotoxicity of the metalaxyl to the treated wheat was the problem, yields would be depressed whether the seed was planted into fumigated or natural soil.

We have also conducted tests on wheat and barley with APRON formulated to include PCNB (TERRACLOR, Uniroyal Chemical) sold under the name of APRON-TERRACLOR. Again, this treatment has provided modest increases in yields of 5–10% where methyl bromide fumigation has resulted in up to 50% higher yields. We have not noticed a yield depression but typically also no yield increase in response to metalaxyl-PCNB.

Treatment of seeds with difenoconazole (DIVIDEND, Ciba-Geigy Corp. Greensboro, N.C.) has provided some yield increases in fields where take-all and Rhizoctonia root rot have been the dominant root diseases. However, the responses have been inconsistent, and growth of spring wheat was depressed by difenoconazole in one field experiment where spring wheat was planted after spring barley. The exact same treated seed of spring wheat planted in the same field but in an area planted the previous year to spring wheat showed a modest yield increase. Again, if the injury associated with difenoconazole was the result of phytotoxicity from the chemical on the seed, the injury would have been evident on the spring wheat after spring wheat as well the spring wheat after the spring barley. Moreover, some form of injury associated with difenoconazole on the seed and evident as poor stands and stunted growth of wheat was widespread in southeastern Washington and adjacent Oregon in the 1995 crop year, with evidence that the injury was caused by increased damage from Pythium.

Biological control is the use of one organism or mixture or organisms to control pests and pathogens of crops. A given biological control organism or mixture of organisms usually works only against the target pest or pathogen on one crop or in one environment with few or no significant effects on nontarget organisms. In contrast, most chemical pesticides work against a wide range of pests or pathogens on several crops and across many environments and can have significant effects on nontarget organisms.

Prior to our present invention, methods available for biological control of fungal pathogens on plants have included bacterial strains of the species Pseudomonas having pathogen-specific activity. Strains of bacteria of the genus Pseudomonas have been reported having potential to grow downward on roots from seed inoculation and to either protect roots of small grain crops against take-all or protect roots and germinating seeds of small grain crops against Pythium. [See U.S. Pat. Nos. 4,456,684 and 4,647,533 to Weller et al.] Strains of Pseudomonas bacteria inhibitory to either *Rhizoctonia solani* or *Pythium ultimum* on cotton have been reported. [See U.S. Pat. No. 5,348,742 to Howell et al.] However, no single Pseudomonas strain has been reported that is effective in controlling several pathogens such as *Gaeumannomyces graminis* and Rhizoctonia and Pythium species simultaneously. The control of only one of the three root diseases is disadvantageous because there is the risk that control of only one disease in a mixture can open the way for increased damage from one or both of the other two diseases in the root disease complex, depending on the site and year. There is also evidence that strains introduced for control of take-all must be able to also compete with Pythium, as a minimum, even if they do not protect against this fungus, or they will be preempted or displaced in the rhizosphere by the rhizosphere-competent Pythium spp.

Prior to the present invention, control of a combination of fungal pathogens of plants by Pseudomonas strains has required a combination of strains with each active against specific pathogens. This has the disadvantages that all strains in the combination may not all function in a given soil or environment, that the strains may compete among themselves, and that combination treatments are more expensive to produce than treatments which include single strains. Alternatively, it has been necessary to combine one or more fungicides with each Pseudomonas strain to obtain the simultaneous control of a combination of pathogens.

The ability to simultaneously control the combination of *G. graminis,* Rhizoctonia, and Pythium, whether with a microorganism or a fungicide is especially difficult because of the broad taxonomic diversity represented by these three groups of fungal pathogens of plants. *G. graminis* is a member of the ascomycotina (a class of fungi), Rhizoctonia is a member of the basidiomycotina (another class of fungi), and Pythium is a member of the oomycetes (still another class of fungi). The ascomycotina, basidiomycotina, and oomycetes are three major and very different classes of fungi, each with fundamentally very different hyphae, both physically and chemically, and with different nuclear condition, and with different physiology.

SUMMARY OF THE INVENTION

The present invention is directed to methods and products useful to simultaneously control the root diseases caused by *Gaeumannomyces graminis,* Rhizoctonia, and Pythium. More particularly, the invention relates to (1) a novel method to identify seed-treatment products for potential to simultaneously control the three kinds of root diseases; (2) microorganism strains having activity against the three kinds of root diseases and methods of obtaining the same, and (3) compositions comprising a fungicide and a microorganism strain, which compositions are useful for field control of the combination of the three kinds of root diseases.

The method for identifying seed-treatment products for potential to control the combination of three root diseases is based on factors designed to apply similar and simultaneous pressure from the three diseases. In brief, the novel method to identify seed-treatment products for potential to simultaneously control Rhizoctonia, *Gaeumannomyces graminis,* and Pythium, comprises planting seeds which have been treated with the test seed-treatment product, directly, i.e., with minimal soil disturbance, into soil cropped continuously to cereals and thus infested with the pathogens which cause the three kinds of root diseases, and identifying those seed-treatment products that control the three kinds of root diseases by increases in yield, plant height, number of emerged plants, length of first true leaf, or leaf dry weight, or decreases in the amount of plant root disease compared to control plants grown from seeds without the test treatment. This method provides a means to evaluate the potential of seed-treatment products to simultaneously control a complex of root diseases, and can be used to test a variety of products, including single biocontrol microorganism strains, combinations of biocontrol strains, and combinations of fungicides and biocontrol strains. The method may be carried out in the field or in the greenhouse using cores of field soil.

The methods to obtain microorganism strains having activity against the three kinds of root diseases include the steps of: (1) isolating root-associated Bacillus spp. strains by collecting roots of seedlings or stubble of the plants of the variety to be protected, which plants have been growing in fields cropped to cereals continuously for at least three years; washing the roots at 4° C. to remove material not tightly adhering to the roots; heat-treating the washed roots to kill bacteria unable to form spores; macerating the heat-treated roots, and dilution plating on a suitable medium; (2) screening the strains isolated in step (1) for inhibitory activity in vitro, first against Rhizoctonia, then individually against *Gaeumannomyces graminis* and Pythium in any order and selecting strains that show inhibitory activity in vitro against all three root diseases; and (3) screening the strains selected in step (2) for disease control in the greenhouse or growth chamber, first against Rhizoctonia, then individually against *Gaeumannomyces graminis* and Pythium in any order, and selecting those strains that show disease control by increases in yield, plant height, number of emerged plants, length of first true leaf, or leaf dry weight, or decreases in the amount of plant root disease compared to control plants grown from seeds without the test treatment. Confirmatory tests may be carried out by growing seeds treated with the strains of step (3) in field soil having a history of all three pathogens.

This method is particularly adapted to identify Bacillus strains having inhibitory activity to all three root diseases, that are well adapted to grow on the roots of cereals at the range of soil temperatures common for cereals in temperate regions of the world where most cereals are grown, that have activity at 4° C., and that form spores suited to long shelf-life. In addition, individual strains of microorganisms obtained by these methods can be combined as a composition with a fungicide, as described, below, to enhance the performance of the fungicide and the strain.

Using our method, we obtained strain L324-92, a novel Bacillus genotype having broad spectrum biocontrol activity against isolates of *G. graminis,* Rhizoctonia, and Pythium. L324-92 showed disease control in the field as evidenced by an increase in the yield of wheat (see Example 1, below).

Any strain intended for biological control of root disease of no-till cereals such as take-all, Rhizoctonia root rot, and Pythium root rot must be adapted to grow at lower temperatures, and our method provides for the selection of strains having such adaptation. Strain L324-92 is the only strain of Bacillus shown to have potential for protection of plants against soilborne plant pathogens that can grow at temperatures down to 4° C.

The invention also comprises compositions useful for field control of the combination of the three kinds of root diseases, which compositions include a fungicide having activity against at least one of the three kinds of root disease, preferably, Rhizoctonia and a Bacillus biocontrol strain having activity against the root diseases caused by *Gaeumannomyces graminis,* Rhizoctonia, and Pythium. These compositions of a biocontrol strain and fungicide provide activity against the full suite of wheat root diseases, and are particularly useful to provide more consistent control of the three kinds of root diseases. As known to those in the art, control of the root diseases can be inconsistent, and there are instances where, for factors not yet identified, field control of root disease may not be accomplished consistently by a fungicide alone or a biocontrol strain alone. Our compositions comprising a Bacillus strain having activity against all three root diseases and a fungicide has been shown to provide consistent field control of the three root diseases.

Further, chemicals to control above ground diseases may be added to the composition.

Disease complexes are common on crop plants, especially root disease complexes, but no prior method has been reported that is based on knowledge required to evaluate the potential of a product to simultaneously control al components in the complex.

Prior to our invention, tests have been conducted with combinations of chemical fungicides and fungal biocontrol agents of individual fungal root pathogens of a crop that could not be fully controlled by either kind of treatment alone. However, the focus of these tests has been to screen for a strain of the biocontrol agent insensitive (resistant) to and therefore compatible with the fungicide so as to increase the number of mechanisms of control applied to the targeted pathogen for an integrated control. Our method uses bacteria naturally insensitive to the chemical selected for use as part of a fungicide-biological control combination to control not just one pathogen, but to simultaneously control the complex of root diseases. This is important because, as known to those of skill in the art, there are instances where control of only one disease in the field can open the way for greater damage caused by one or more of the other root diseases.

Our products are also compatible with other fungicides used for control of other diseases as part of an integrated pest management (IPM) system. For example, seeds of wheat typically are treated with a fungicide to control seedborne and some soilborne spores of smut fungi, especially *Tillia caries* and *Urocystis agropyri* responsible, respectively, for common bunt and flag smut. Our bacteria intended for use in our biological-chemical combinations for the simultaneous control of cereal root pathogens are naturally insensitive and therefore fully compatible with other fungicides needed by growers to control smut and other diseases.

Prior to our method, companies with seed-treatment products sold as mixtures have combined two or more chemicals or a chemical+biological control agent for protection of germinating seeds, such as cotton and peanuts, against damping off caused by Pythium and/or Rhizoctonia species. The manufacturer of difenoconazole and metalaxyl provides these two chemicals as a mixture to control the seed-infecting/damping-off phases of as many pathogens as may be sensitive to these two relatively specific fungicides, including smut fungi and Pythium spp. Metalaxyl controls only Pythium infection of germinating seeds and difenoconazole controls smut diseases and provides some protection against Rhizoctonia spp. that may attack the seeds and roots of seedlings. However, these existing products do not simultaneously control the full combination of cereal root diseases favored by continuous no-till management systems. Our products, including our fungicide-biological control agent combinations, can be screened using the method described above and selected for the simultaneous control of the full suite of cereal root diseases, while allowing for the safe addition of other chemicals to control of above-ground diseases as well and if necessary.

Our invention applies to all management systems but is based on and is developed specifically for cereal planted directly (no-till) into its own stubble (wheat following wheat, barley following barley, etc., with little or no crop rotation) and harvest residue left standing or lying undisturbed on the soil. The invention can be used to reduce the effects of all three root diseases known to affect cereals under these conditions.

Further, our combination fungicide and microorganism compositions are active against the full suite of wheat root diseases, while allowing for the safe addition of other chemicals to control of above-ground diseases as well and if necessary. Further, our compositions comprising a Bacillus strain having activity against all three root diseases and a fungicide has been shown to provide consistent field control of the three root diseases, in areas where consistent control was not obtained used either a fungicide alone or biocontrol strain, alone.

In accordance with this discovery, it is an object of the invention to provide methods for identifying seed-treatment products for potential to simultaneously control root diseases caused by *Gaeumannomyces graminis,* Rhizoctonia, and Pythium species. Another object of the invention is the provision of spore-forming microorganism strains, i.e., Bacillus spp., having activity against the three kinds of root diseases, and methods of obtaining these strains. Microorganisms obtained by our methods can form spores suited to long shelf life when formulated for use as biocontrol agents. They can establish and persist for at least six months in the rhizosphere when introduced with seeds or other planting material at the time of planting, and they can grow at temperatures as low as 4° C. In addition, individual strains of microorganisms obtained by these methods combined as a composition with a pathogen-specific fungicide such as difenoconazole, can under pressure from a combination of pathogens, including one or more pathogens insensitive to the pathogen-specific fungicide, enhance the performance of the fungicide and perform better themselves as indicated by increased growth or yield response of the crop treated with the fungicide-microorganism composition.

A further object of the invention is the provision of novel compositions which includes a fungicide and biocontrol microorganism, which compositions are useful for field control of the combination of the three kinds of root diseases.

Other objects and advantages of the invention will become readily apparent from the ensuing description.

BRIEF DESCRIPTION OF THE DRAWINGS

FIG. 1 shows a protocol for selecting Bacillus spp. with biocontrol activity against *R. solani* AG8, *G. graminis* var. *tritici* and Pythium spp.

FIG. 2 shows suppression of Pythium root rot by Bacillus spp. measured as percent seedling emergence (A) and length of the first true leaf (B).

FIG. 3 shows comparison data of the growth of Bacillus sp. L324-92 (A) and *Bacillus subtilis* A13 (B) at 10, 15, and 20° C. The vertical bars represent standard deviations with three replicates.

FIG. 4 shows emergence data for wheat seedlings grown in the greenhouse in field soil that contained the three root pathogens. The treatments included fungicides alone (difenoconazole or difenoconazole plus metalaxyl), microorganism strains alone (Bacillus sp. L324-92 or *P. fluorescens-putida* Q69c-80), and combinations of microorganism and fungicide. The check denotes untreated seedlings.

DETAILED DESCRIPTION OF THE INVENTION

The present invention provides methods and compositions useful to simultaneously control the root diseases caused by *Gaeumannomyces graminis* (Gg), Rhizoctonia, and Pythium. In a first embodiment, methods are disclosed for identifying seed-treatment products for potential to simultaneously control the three kinds of root diseases. In a second embodiment, novel microorganism strains having activity against the three kinds of root diseases and methods of obtaining the same are described. A third embodiment comprises compositions which include at least one chemical fungicide in combination with at least one microorganism strain having activity against the three kinds of root disease, which composition is useful for field control of the combination of the three kinds of root diseases.

Methods for Identifying Seed-Treatment Products For Potential to Control the Combination of The Three Root Diseases The first embodiment comprises methods for identifying seed-treatment products for potential to simultaneously control the three kinds of root diseases. The method for identifying seed-treatment products for potential to control the combination of three root diseases is based on factors designed to apply similar and simultaneous pressure from the three diseases, and it works either in the field or in the greenhouse. In this method soil is used that has been cropped continuously to a crop susceptible to the targeted root diseases, for example, continuous wheat, continuous barley, or mixtures of wheat and barley, to provide every opportunity for the presence of high populations of the root pathogens responsible for the three root diseases of these crops. The soil is chosen from a site with soil pH, clay content and other soil conditions that are overlapping in terms of suitability to each of the three root diseases, to assure maximal but more or less equal activity or pressure from each of the three. Crop seeds for the crop for which disease control is desired, e.g., wheat seeds, are treated with the test seed-treatment product and planted into the soil with minimal disruption. For example, the wheat seeds are direct drilled into the soil, as opposed to planting into tilled soil, to assure minimum disturbance and therefore maximum activity of the root pathogens. If any one of these three factors is omitted, e.g., the soil is from a field cropped the previous year to a plant species other than a cereal, the soil is disturbed by conventional type tillage, or the soil is too acid for take-all or not conductive to Pythium root rot such as to favor less than all three root diseases, the evaluation will give false positives. In other words, if only one or two of the three root diseases are active, the method cannot be expected to work, or it will reveal potential for products that will work only partially or inconsistently.

Typically, soil conditions favorable for substantially more or less equal and simultaneous pressure from the root diseases caused by *Gaeumannomyces graminis*, Rhizoctonia, and Pythium are the following: a soil pH of about 5 to 6, a clay content of less than about 20%, a soil temperature ranging from about 5 to 15° C., and a soil moisture status near field capacity.

As a typical test in the field, seeds treated with the test seed-treatment product are planted directly (no-till) into undisturbed soil and residue of the previous crop, with all nitrogen, phosphate, and sulfate provided as a fertilizer solution below the seed at the time of planting. Nitrogen rates are based on soil tests and projected yield goals as a standard agronomic practice. A convenient field plot size is individual plots of 24 feet long and eight feet wide, with eight rows spaced 12 inches apart, however, larger or smaller plots would also suffice for this kind of test. For statistical data, it is preferred that each treatment is replicated at least four times in a randomized complete block design. Glyphosate (ROUND-UP) is applied in time to allow at least 14 days between application of the herbicide and planting. Other herbicides are applied as necessary throughout the growing season for broad-leaf weed and wild oat control. Effective seed treatment products are identified on the basis of comparisons of the growth of treated plants to the growth of control (nontreated) plants, e.g., increased growth, decreased root disease or both. Parameters measured can include emergence, plant height, length of first true leaf, number of heads, fresh or dry weight, and grain yield. Root disease is assessed directly by counting the number of seminal and crown roots and determining the number with symptoms typical of take-all and Rhizoctonia root rot. Disease can also be assessed by evaluating the overall severity of take-all or Rhizoctonia root rot on a disease scale from 0 to 8, where 0=healthy plant and 8=plant dead or nearly so.

As a typical test in the greenhouse, cores of soil from a field continuously cropped to cereals to provide every opportunity for the presence of high populations of the root pathogens responsible for the three root diseases are dug out of the stubble row and brought in from the field and planted as soon as possible to maintain the pressure of the disease organisms as they were in the field. Placement of the soil cores and planting of the seeds is carefully carried out so as to minimize disturbance of the soil to maximize activity of the root pathogens. A convenient soil core size is a 6-inch diameter, 6-inch deep core which can be conveniently put into a 6-inch diameter pot. It is preferred that the soil cores brought in from the field are planted as soon as possible to maintain the pressure of the disease organisms as they were in the field. Immediately after the cores are brought in they are watered to the equivalent of field capacity in order to promote the germination of volunteer seed deposited at harvest. Once the volunteer germinates it is killed with a herbicide, preferably glyphosate. Ten seeds are sown in each pot at a depth of about 1 cm and plants are grown for 4 to 6 weeks. Pots are watered once a week or as needed with a nutrient solution containing only macroelements. Each treatment consists of five to seven replicate pots with six the preferred number of replicates. Effective seed treatment products are identified on the basis of comparisons of the growth of treated plants to nontreated control plants. Parameters measured can include emergence, plant height, length of first true leaf and fresh or dry weight. Root disease is assessed directly by counting the number of seminal and crown roots and determining the number with symptoms typical of take-all and Rhizoctonia root rot. Disease can also be assessed by evaluating the overall severity of take-all or Rhizoctonia root rot on a disease scale from 0 to 8, where 0=healthy plant and 8=plant dead or nearly so.

Testing in the greenhouse offers the advantage of having the ability to maintain growth variables more constant than in a field situation, for example, maintain the temperature in the desired range, to maintain the soil moisture status near field capacity, to thereby optimally identify seed-treatment products for potential to simultaneously control the three kinds of root diseases.

Our novel method is useful to evaluate various potential seed-treatment products for control of the three root diseases. Such products can be single biocontrol microorganism strains, combinations of biocontrol strains, and combinations of fungicides and biocontrol strains.

Application of the test seed-treatment to the seed is carried out by standard methods as known to those in the art. We have found generally the application of about $10^4$ to $10^8$ bacteria per seed (colony forming units) and preferably about $10^6$ to $10^8$ bacteria per seed (CFU) is suitable for testing individual strains or combinations of strains. The fungicide is applied at the normal recommended rate.

The novel method to identify seed-treatment products for potential to simultaneously control the three kinds of root diseases is described firer in Example 5, below. As shown in Table 6 and FIG. 4, seedling vigor (as measured by the size of wheat seedlings) and emergence data of wheat seedlings indicated the potential of seed-treatment products to simultaneously control the three root diseases. A key to this discovery of new seed-treatment products rests with our discovery of the method of this embodiment to test for activity against all three root diseases in a single test.

Novel Microorganism Strains Having Activity Against The Three Kinds of Root Disease and Methods to Obtain The Strains A second embodiment of the invention are novel microorganism strains having activity against a combination of the root diseases caused by *Gaeumannomyces graminis*, Rhizoctonia, and Pythium, and methods for selecting the same. In this method strains are screened sequentially for activity against the three kinds of root disease under controlled conditions. Our method adds additional procedures over prior art screening methods to assure that the strain (1) is well adapted to grow on the roots of wheat at the range of soil temperatures common for wheat in temperate regions of the world where most wheat and barley is grown, and particularly at temperatures as low as 4° C., (2) forms spores suited to long shelf-life for when treated seeds are stored in a warehouse before planting, and (3) is inhibitory to fungi responsible for the three root diseases.

The first procedure, added to assure that the microorganism strain, e.g., Bacillus strain, is adapted to grow on roots of wheat at a wide range of temperatures, has two parts. In brief, in our method, test microorganism strains are collected from roots from young plants of a variety to be protected from the three kinds of root disease, e.g, wheat, which have been growing in commercial fields where the cereal crop, e.g., wheat, has been grown continuously (no crop rotation) for at least three years. Thus, the likelihood is high that the soil microflora enriched by repeated exposure to the roots of wheat will include populations adapted to the roots of wheat. Second, the roots dug from these fields are washed in sterile water or buffer at 4° C. sufficient to remove any material not tightly adhering to the roots, and then these washed roots are macerated and used as the source of root-adapted strains of microorganisms. Generally, four washes is sufficient to remove material that is not tightly adhering to the roots.

The second procedure, added to assure that the strain can form spores for long shelf life, involves the standard procedure used to isolate spore-forming bacteria, namely, serial dilutions of the root macerates in sterile water are heat treated to kill bacteria unable to form spores and selectively leave spore-forming bacteria, e.g, in a water bath at 80° C. for at least 10 minutes, before dilution plating on a suitable medium, e.g., tryptic soya agar.

The third procedure, added to assure that the strain is inhibitory to the fungi responsible for the three wheat root diseases, involves two steps: a succession of standard tests for antibiosis on agar in petri plates followed by screens for ability to suppress individual root diseases on wheat growing in soil in containers in the greenhouse. For the first step, random isolates from the dilution plates are tested first for ability to produce antibiotics inhibitory to Rhizoctonia. Isolates positive in this test are then tested in agar plates for inhibitory activity against *G. graminis* and separately for inhibitory activity against Pythium, for example, isolates which have the ability to produce antibiotics against *G. graminis* and then against Pythium. For the second step, isolates positive on agar against Rhizoctonia, *G. graminis*, and Pythium are tested in the greenhouse or growth chamber for control of disease caused by Rhizoctonia. Those positive in this test are then tested in the greenhouse or growth chamber for individual control of the diseases caused by *G. graminis*, and Pythium. Strains selected are denoted as having activity against the three kinds of root diseases.

Confirmatory tests may be carried out by growing seeds treated with the selected strain in field soil with a history of all three pathogens, as described in detail, below.

The method can be summarized as follows:

1. Isolate root-associated Bacillus spp. as follows:

(a) Collect roots from seedlings or stubble from fields cropped continuously (at least three years) to a crop susceptible to the targeted root diseases, for example, continuous wheat, continuous barley, or mixtures of wheat and barley.

(b) Wash the roots in sterile water or buffer (e.g., phosphate buffer) at 4° C. to remove material not tightly adhering to the roots. For convenience of handling, the roots may be cut into sizes convenient for washing in tubes. Generally four washes is sufficient to remove material that is not tightly adhering to the roots.

(c) After the last wash, transfer the roots to fresh sterile water or buffer and heat at a time and temperature sufficient to kill bacteria unable to form spores. In general, heating at 80° C. for 10–30 minutes is suitable.

(d) Macerate the heat-treated roots.

(e) Make up to a known volume with buffer, and dilution plate the root macerates on a suitable medium, i.e., prepare serial dilutions of the root macerates, and plate dilutions onto tryptic soya agar to isolate individual strains.

Alternatively, the roots may be macerated prior to heat-treatment and dilution plating.

2. Screen the strains isolated in step (1) for inhibitory activity in vitro against Rhizoctonia, *Gaeumannomyces graminis* and Pythium as follows:

(a) first, screen the test strain for inhibitory activity in vitro against Rhizoctonia by growing the test strain on a suitable medium in the presence of Rhizoctonia, e.g., *Rhizoctonia solani* AG8, and select those strains that show inhibitory activity as measured by a zone of inhibition between the test strain and the test fungus, preferably at least about 2 mm.

(b) screen the strains selected in step (2)(a) for inhibitory activity in vitro against *Gaeumannomyces graminis* and Pythium individually, in any order of sequence, by growing the test strain on a suitable medium in the presence of *Gaeumannomyces graminis*, e.g., *G. graminis* var. *tritici*, and growing the test strain on a suitable medium in the presence of Pythium, e.g., *P. irregulare*, and selecting those strains that show inhibitory activity as measured by a zone of inhibition between the test strain and the test fungus, preferably at least about 2 mm.

(3) screen the strains selected in step (2) for biocontrol activity in vivo in the greenhouse or growth chamber as follows:

(a) first, screen the test strain for biocontrol activity against Rhizoctonia by growing seeds of crops susceptible to the three root diseases, e.g., cereal crops or grain legumes, which seeds have been treated with the test strain, in soil in the greenhouse or growth chamber in the presence of Rhizoctonia, e.g., *R. solani* AG8, for sufficient time, e.g., 3–4 weeks, to test the activity of the test strain, and select those strains that show biocontrol activity as measured by reduction of roots disease (Rhizoctonia root rot), or increases in seedling emergence, plant height, first true leaf or other standard measure compared to control plants grown from seeds without the test strain.

(b) screen the strains selected in step (3)(a) for biocontrol activity against *Gaeumannomyces graminis* and Pythium individually, in any order, by growing seeds treated with the test strain in soil in the greenhouse or growth chamber in the presence of *Gaeumannomyces graminis*, e.g., *G. graminis* var. tritici, for sufficient time, e.g., 3–4 weeks, to test the activity of the test strain, and growing seeds treated with the test strain in soil in the greenhouse or growth chamber in the presence of Pythium, e.g., soil infested with Pythium spp., and selecting those strains that show biocontrol activity as measured by reduction of root disease (take-all or Pythium root rot), or increases in seedling emergence, plant height, length of first true leaf, or other standard measure compared to control plant grown from seeds without the test strain.

The screening procedures are carried out using in vitro and greenhouse protocols known in the art. For example, U.S. Pat. Nos. 4,456,684 and 4,647,533 to Weller et al. and U.S. Pat. No. 5,348,742 to Howell et al., which are incorporated herein by reference, describe standard in vitro testing procedures, treatment of seeds with test microorganisms, production of inoculum of the pathogens, and soil amendments.

Confirmatory tests may be carried out by growing seeds with the strains selected in step (3) (b) in field soil having a history of all three pathogens, and evaluating disease control by increases in yield, plant height, number of emerged plants, number of heads, length of first true leaf, or leaf dry weight, or decreases in the amount of plant root disease compared to control plants grown from seeds not treated with the test strain. Tests in field soil may be carried out in the greenhouse or growth chamber by growing the treated seeds in soil cores dug out of the stubble row and brought in from the field or by growing the treated seeds in the field.

Using our method, we discovered Bacillus strain L324-92 having activity against all three kinds of root diseases. This is described in Example 1, below. Strain L324-92 is one strain out of about 2000 selected randomly from dilution plates at the beginning of the process that has ability to inhibit all three kinds of pathogens on agar and suppress all three root diseases on wheat growing in the greenhouse. In addition, this strain has been shown to be unique among strains of Bacillus species in that it can grow at temperatures between 4 and 40° C.

Of 300 strains tested in the growth chamber, strain L324-92 was isolated having broad spectrum biocontrol activity that suppresses Rhizoctonia root rot, take-all, and Pythium root rot. In the field shown in Example 1, below, it increased the yield of wheat by an average of 23%. This strain is of particular interest because other known biocontrol agents are not effective against all three diseases. Further, L324-92 is effective at a population of one to two orders of magnitude less than Pseudomonas biocontrol agents.

A detailed morphological, physiological, and biochemical description of strain L324-92 is presented in Example 2, below. Example 3, below, shows the spectrum of in vitro inhibitory activity of Bacillus sp. L324-92 against fungal root pathogens. Strain L324-92 is inhibitory to all 36 isolates of *G. graminis* var. *tritici* tested, all 46 isolates of Rhizoctonia spp. tested, and all 13 isolates of Pythium spp. tested.

Any strain intended for biological control of root diseases of no-till cereals must be adapted to the cold soils typical of fields in temperate areas in the late fall or early spring with soils insulated from the sun's rays by surface residues. Example 4, below, and FIG. 3, describe the influence of temperature at 10, 15 and 20° C. on the growth of Bacillus strains L324-92 and the known prior art strain, *B. subtilis* A13, the most well known Bacillus strain. The results show that Bacillus sp. L324-92 grew better than *B. subtilis* A13 at 15 and 20° C. and only L324-92 (not A13) grew at 10° C. In another test, L324-92 grew at temperatures as low as 4° C., with doubling time of 55.2 h between 7 and 14 days after inoculation. Thus, strain L324-92 not only is taxonomically very different from A13, it also differs in its ability to grow at 4° C., compared with A13, which does not grow at temperatures below 10° C. No other strain of Bacillus shown to have potential for protection of plants against soilborne plant pathogens has been reported to grow at temperatures down to 4° C. Strain L324-92 can grow at temperatures ranging from 4 to 40° C.

Strain L324-92 was deposited under terms of the Budapest Treaty in the Agriculture Research Culture Collection (NRRL), Peoria, Ill., on Feb. 5, 1996, and has been given the accession number NRRL B-21525.

A microorganism strain selected by our method provides biological control of soilborne pathogens of cereals and grain legumes, including *Gaeumannomyces graminis* var. *tritici*, Pythium spp., and *Rhizoctonia solani*. Strains selected by our method can be used to control these root diseases on any crop that is susceptible to these diseases. Examples of such crops are cereal crops, including wheat, barley, triticale, and rye, and grain legumes, including chickpea, soybean, and corn. Suppression of these pathogens results in a significant increase in the yield of these crops. The biocontrol strain can be applied to the plant as a seed treatment or root dip, e.g., dipping roots of transplant plants, using standard methods as known to those in the art. Such methods are described in U.S. Pat. Nos. 4,456,684 and 4,647,533 to Weller et al., which are hereby incorporated by reference. Suitable agricultural carriers or sticking agents, e.g., methylcellulose, or diluents, e.g., water or weak salt solutions, may be used for application of the biocontrol strain to seeds or for preparation of the root dip.

The biocontrol strain is applied in an effective amount, that is, in an amount sufficient to suppress (reduce the incidence or severity of) the target diseases compared to control plants grown without the biocontrol strain. This assumes that factors such as water, fertilizer, soil and air temperatures are not limiting to the growth of the target crop. We have found generally the application of about $10^4$ to $10^8$ bacteria per seed (colony forming units) is effective. Optimal protection generally occurs with about $10^6$ to $10^8$ bacteria per seed (CFU). The biocontrol strain can be spores or vegetative cells. An effective amount in a particular case can readily be determined by trials runs as known in the art.

In sum, our methods include a unique combination of procedures to obtain strains having inhibitory activity to all three root diseases, that are well adapted to grow on the roots of cereals at the range of soil temperatures common for cereals in temperate regions of the world where most cereals are grown, have activity at 4° C., and form spores suited to long shelf-life. For example, in our protocol, roots are washed at 4° C., macerates of washed roots rather than root washings are dilution plated as a source of microorganisms, roots selected from a series of washings are heat-treated to select only endospore-forming bacteria, and candidate isolates are screened against all three target pathogens.

Composition of Fungicide and Biocontrol
Microorganism For Field Control of the Three
Kinds of Root Diseases A third embodiment of our invention comprises novel compositions which include a fungicide and biocontrol microorganism, which composition is useful for field control of the combination of the three kinds of root diseases. The combination is intended to bring about one or more of the following effects: (1) enhanced activity and persistence of the biological component through elimination of competition around the seed and in the rhizosphere by the chemical component; (2) greater stability of control, including, less risk of one root disease not controlled by a chemical or biological component alone becoming more destructive in response to control of one or more of the other root diseases in the complex; (3) earlier and longer-lasting control, achieved by the immediate protection provided with the chemical component and on-going protection provided with the biological component; (4) broader-spectrum control, owing to the combined activity of the biological and chemical components.

More than one fungicide may be included in the composition, however, all must be compatible with the biocontrol strain, and a critical feature of at least one of the fungicides in the composition is that it have activity against at least one of the three kinds of root disease, and preferably, have activity against Rhizoctonia. Microorganism strains used in the composition have activity against all three pathogens that cause the three kinds of root diseases, for example, Bacillus strains obtained by the selection method described above, in the second embodiment of this invention.

Surprisingly, this combination of the chemical fungicide and microorganism, has the ability to control the combination of the three kinds of root disease in the field. This is advantageous because there is the risk that control of only one disease in a mixture can open the way for increased damage from one or both of the other two diseases in the root disease complex, depending on the site and year.

The amount of chemical fungicide in the composition is that sufficient to control root disease, preferably, Rhizoctonia. The microorganism is added to the composition in an amount effective to control root disease, as discussed above. Other ingredients which do not detrimentally affect the activity of the fungicide and microorganism strain can be added as known to those in the art. The composition is applied in an effective amount, that is, in an amount sufficient to suppress (reduce the incidence or severity of) the target diseases compared to control plants, as discussed above.

As discussed in detail in Example 6, below, exemplary of the combination of chemical fungicide and bacteria discovered with potential to control the combination of three root diseases of wheat includes the fungicide difenoconazole, sold under the trade name of DIVIDEND (Ciba-Geigy Corp. Greensboro, N.C.), (a fungicide reported to have activity against Rhizoctonia species and against take-all but has no known activity against Pythium root rot) combined as provided from the manufacturer with a suspension of cells of Bacillus sp. L324-92 grown in the laboratory. This combination is referred to as Bonanza 1 in Example 6. The composition may be applied wet to the seeds of wheat and the seeds then dried before planting. For test purposes, a composition comprising difenoconazole and *Pseudomonas fluorescens-putida* strain Q69c-80, a strain active against *G. graminis* and Pythium, but not against Rhizoctonia, was included in the test presented in Example 6, below. This combination (denoted as Bonanza 2) passed the method of the first Embodiment, described above, which identifies seed-treatment products for potential to control the combination of the three root diseases. Strain Q69c-80 was selected according to the claims outlined in U.S. Pat. No. 4,456,684, and was deposited under terms of the Budapest Treaty in the Agriculture Research Culture Collection (NRRL), Peoria, Ill. on Feb. 5, 1996, and has been given the accession number NRRL B-21526.

The results, presented in Table 7, below, show that the combination fungicide and biocontrol strain products outperformed the fungicide alone or biocontrol strain alone.

As discussed above, prior to our method, tests have been conducted with combinations of chemical fungicides and microbial antagonists of pathogens to control root diseases of crop plants that could not be controlled by either kind of treatment alone. However, the focus has been on integrated control of one disease or pest species and not the simultaneous control of all components of a disease complex. Disease complexes are common on crop plants, especially root disease complexes, but no prior method has been reported that is based both on knowledge required to simultaneously evaluate all components in the complex. Our discovery marks a significant advance in the art of control of root diseases. The composition of the invention is useful in all cereal-growing areas, including the combination of wheat and barley root diseases favored by continuous no-till management systems. Our products are active against the full suite of wheat root diseases, while allowing for the safe addition of other chemicals to control of above-ground diseases as well and if necessary.

In sum, our invention is the first report of methods to screen seed-treatment products and apply them for the simultaneous control of the combination of take-all, Rhizoctonia root rot, and Pythium root rot. Current methods for evaluation of seed-treatment products are done in fields without regard to conditions likely to favor the full suite of root diseases. The invention is useful in that seed-treatment products with potential to control all three root diseases simultaneously during growth and development of the wheat or barley are needed for achieving the high yields and greater production efficiency possible with no-till compared with conventional wheat and barley production systems.

EXAMPLES

The following examples are intended only to further illustrate the invention and are not intended to limit the scope of the invention which is defined by the claims.

EXAMPLE 1

This example describes our method of screening to select microorganism strains having activity against the three kinds of root disease.

We isolated Bacillus spp. closely associated with wheat roots by repeated washings of roots and dilution plating of heat-treated suspensions. The isolated bacteria were then screened in vitro and in the growth chamber and tested in the field for their biocontrol activity against Rhizoctonia root rot, take-all and Pythium root rot.

In particular, wheat seedlings in the 1- to 3-leaf stage were collected from fields near Lind and Pullman, Wash. that had been cropped annually to wheat for 25 and 12 years, respectively, after decades of wheat/fallow or wheat in various crop rotations. Roots were repeatedly washed to select for those strains that could adhere tightly to the root surface as follows: fragments of four seminal roots (0 to 2.5 cm from the seed and 5 to 8 cm deep, depending on the depth of sowing) were excised and then washed four times (each 30 minutes) with 50 ml of fresh sterile water in a 250-ml flask on a rotary shaker (250) rpm in a 4° C. area of the cold room. Washed root segments were placed in a test tube with 5 ml of 0.0125 M phosphate buffer (1.21 g $KH_2PO_4$, 2.80 g $K_2HPO_4$, 1 liter deionized water; pH 7.1) and heat-treated at 80° C. for 30 minutes in a water bath. Heat-treated root segments were macerated in a mortar, resuspended in 5 ml of phosphate buffer, and aliquots (100 $\mu$l) from a serial dilution were plated on 1/10 tryptic soy agar (1/10 TSA) for single colony isolation. Individual colonies were restreaked on suitable media to assure purity. Individual pure isolates were stored in 40% glycerol at −80° C.

In vitro inhibition was assayed on 1/10 TSA, 1/5 strength potato dextrose agar (40 g potato, 4 g dextrose, 15 g agar, 1 L distilled water), and 1/5 strength nutrient broth yeast extract agar. Approximately 2,000 colonies (1,500 isolates from the Lind site and 500 isolates from the Pullman site) were selected for testing. To screen for in vitro antibiosis, four isolates were spotted with sterile toothpicks around the edge of a plate of 1/10 TSA. Plates were incubated for 2 days at 15° C., and one 8-mm-diameter agar disk of R. solani AG8 isolate from a 1-week-old PDA culture was placed in the center of the plate. After incubation another week, the width of the inhibition zone between each bacterial colony and the fungal colony was measured. Of the original 2000 isolates, 310 isolates showed inhibition to R. solani AG8. Of the 310 isolates, approximately 172 were also inhibitory in vitro to Gaeumannomyces graminis var. tritici and P. irregulare.

Initial screenings for biocontrol activity were conducted in a growth chamber using a tube assay similar to that described by Ownley et al. (*Phytopathology* 82:178–184 (1992)). The assay used plastic tapered tubes (2.5-cm diameter×16.5-cm long) with holes at their bottoms that were supported in a hanging position in a plastic rack. Each tube was plugged with a cotton ball and then filled half full with sterile vermiculite followed by 10 g of either steamed or raw soil infested with oat-kernel inoculum of G. graminis var. tritici or R. solani AG8. When Rhizoctonia root rot was the target disease, one whole oat kernel colonized with R. solani AG8 isolate was placed on the top of 10 g of soil in tubes and covered with another 10 g of the same soil. When take-all was the target disease, 10 g of soil infested with 1.0% (w/w) oat-kernel inoculum (particle size: 0.25–0.5 mm) of G. graminis var. tritici was placed on top of the vermiculite. Each tube was immediately watered with 10 ml of tap water amended with metalaxyl (RIDOMIL 0.075 g/liter; Ciba Geigy corp., Greensboro, N.C.) to inhibit indigenous Pythium spp. Tubes were preincubated 7 days before planting in tests with Rhizoctonia root rot and 2 days in tests with take-all. For both kinds of tests, two wheat seeds were placed on the soil surface in each tube and covered with another 2-cm-thick layer of sterile vermiculite.

Wheat seeds were disinfected by immersing them in a 25% (w/v) solution of commercial bleach (5.25% sodium hypochlorite) for 3 minutes, rinsed for 30 minutes under running tap water, dried under a stream of sterile air, and stored at room temperature in a plastic bag. Wheat seeds were coated with commonly used methods (Pierson and Weller, *Phytopathology* 84:940–947 (1994)). Bacteria cells were grown as a lawn on NBY agar medium for 48 hours at 21–24° C. Four ml of a 0.5% (w/v) suspension of methylcellulose was added to each plate, and the cells were scraped free so they became suspended in the methylcellulose. The methylcellulose suspension with bacterial cells was mixed with 10 g (ca. 180 seeds) of seed in a Petri dish, and the coated seeds were dried for 30 minutes under a stream of sterile air. Populations sizes ranged from 10 to $10^7$ CFU per seed as determined by shaking coated seed in sterile water or buffer for 20 minutes followed by dilution plating.

After sowing, each tube received an additional 5 ml of tap water, and the racks of tubes were then returned to a growth chamber with a 12-h photoperiod and a constant 15° C. For the first week, each tube received 5 ml of tap water twice (days 3 or 4 and 6 or 7) after planting, and thereafter 5 ml of 1/3 (v/v) strength Hoagland's solution twice per week. After 3–4 weeks, roots of wheat seedlings were washed free of the rooting medium, and disease was evaluated. Emergence and shoot length (measured on washed seedling from the position of the remnant seed piece to the tip of the longest leaf) was determined for each test.

Severity of Rhizoctonia root rot was evaluated on a scale of 0–8, where: 0=no lesion evident; 1=<50% roots with a single typical brown sunken lesion; 2=<50% roots each having a few brown sunken lesions; 3=>50% roots each with one or more brown sunken lesions; 4=<50% roots with brown sunken lesions within 1 cm from the seed; 5=>50% roots with brown sunken lesions within 1 cm from the seed; 6=>50% roots shorter than 3 cm (inoculum line) from the seed; 7=>50% roots shorter than 1 cm from the seed; 8=almost no roots with stunting or death of seedling. Severity of take-all was evaluated on the 0–8 scale (Ownley et al., 1992, supra), where: 0=no disease evident; 1=<10% root area with black lesions; 2=10–25% root area with black lesions; 3=>25% root area with black lesions and one root with lesions at base of stem; 4=more than one root with lesions at base of stem; 5=all roots with lesions at base of stem, at least one lesion on lower stem, but no chlorosis; 6=many lesions on stem and the first true leaf chlorotic; 7=all leaves chlorotic and plant severely stunted; 8=plant dead or nearly so.

Tests with Pythium root rot used 9.5-cm-diameter pots filled with 200 cc of sterile vermiculite followed by 300 g of a field soil naturally infested with Pythium spp. spores. Each pot received 100 ml of tap water and was incubated for 2 days at room temperature prior to planting. Seven seeds were sown about 2 cm deep in each pot and covered with 100 cc of vermiculite. Each pot received 50 ml of tap water and then was incubated at 15° C. for 4 weeks in a growth chamber Each pot received 50 ml of 1/3 v/v Hoagland's solution once each week. Emergence, shoot height and length of the first true leaf of wheat seedlings were recorded.

All experiments were conducted with Thatuna silt loam (TSL) obtained from a plot cropped every second or third year to wheat on the Washington State University Plant Pathology Research Farm, Pullman. The soil was collected from the top 10–15 cm layer of the soil profile and passed through a 0.5-cm-mesh screen. Steamed soil refers to moist soil that was treated at 95° C. for 80 minutes using air mixed with steam. Raw soil refers to the same soil with heat treatment. Soils were prepared 1 week prior to each experiment and air-dried at room temperature.

In all experiments, treatments were arranged in a randomized complete block with five replicates of steamed and raw soil, respectively. Effect of all seed treatments were analyzed by the SAS general linear model procedure (SAS Institute, Cary, N.C.), and treatment means were separated by Fisher's protected LSD at P=0.05.

Confirmatory field tests were carried out. Two field tests were conducted in 1993 in a field near Dusty, Wash., naturally infested with the pathogens responsible for take-all, Rhizoctonia root rot, and Pythium root rot. At one site wheat (cv. Penawawa) were sown directly (no-till) into standing spring barley stubble (SBS) and at the other site into spring wheat stubble (SWS). Except for these cropping histories, the two sites were identical. Strains L324-92 and P206-92 were applied at approximately $3.5×10^6$ and $9.7×10^6$ CFU per seed, respectively.

Treatments were arranged in a randomized complete block design with 4 replications for SWS and five replications for SBS. Each treatment plot consisted of eight, 8-m long rows spaced 30 cm apart. Yields were obtained by harvesting the five center rows out of each eight-row plot. Effect of the seed treatment was analyzed by the SAS general linear model procedure (SAS Institute, Cary, N.C.), and treatment means were separated by Fisher's protected LSD at P=0.05. Control plots included nontreated seed and seed treated with a 1.5% methylcellulose suspension sown into raw soil and nontreated seed sown into plots fumigated with methyl bromide.

A summary of the screening procedure and confirmatory field test protocol is shown in FIG. 1.

RESULTS

1. Isolation of root-associated Bacillus spp.

The total detectable bacterial population ranged from $2.0 \times 10^5$–$5.1 \times 10^6$ CFU/cm of root with attached soil. Repeated washings followed by heat treatment decreased the bacterial population on the roots to 21–120 CFU/cm. Qualitatively, the dominant colony types of bacteria after 4 washings were different from those before washing.

2. In vitro antifungal activity

Of about 2000 bacterial isolates, about 300 inhibited the growth of *R. solani* AG8 in vitro. Of those inhibitory to *R. solani* AG8, all were inhibitory to *G. graminis* var. *tritici* on all the media used, and about 172 were inhibitory to *G. graminis* var. *tritici* and *P. irregulare*. Strain L324-92 inhibited all three test pathogens, but strains L331-92 and P206-92 did not inhibit *P. irregulare*.

3. Biocontrol activity in growth chamber tests

Figure 2B:
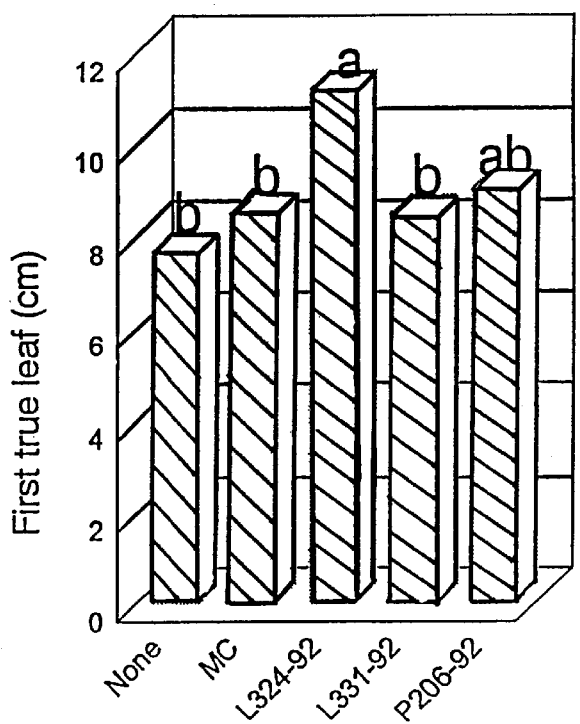

About 300 strains of Bacillus spp. that inhibited both *R. solani* AG8 and *G. graminis* var. *tritici* in vitro were screened for suppression of Rhizoctonia root rot by the tube assay in the growth chamber. Eighteen of these strains were then tested for ability to suppress take-all. Three strains were consistently suppressive to both pathogens (Table 1). When these three strains were tested against Pythium spp. in natural soil, only L324-92 resulted in significantly higher seedling emergence and longer first true leaf, both of which are responses to Pythium control (FIG. 2). The results in Table 1 and FIG. 2, taken collectively, show that strain L324-92 is active against each of the three root diseases.

TABLE 1

Effect of seed treatment with Bacillus strains on suppression of Rhizoctonia root rot caused by *R. solani* AG8 and take-all caused by *G. g. tritici* in the growth chamber assays

| Seed treatment[a] | Disease Severity[b] |
|---|---|
| Rhizoctonia root rot[c] | |
| Nontreated | 4.69 A[d] |
| Methylcellulose | 4.50 A |
| L324-92 | 3.62 B |
| L331-92 | 3.55 B |
| P206-92 | 3.60 B |
| Take-all[e] | |
| Nontreated | 3.92 A |
| Methylcellulose | 3.69 A |
| L324-92 | 2.80 C |
| L331-92 | 3.13 B |
| P206-92 | 2.76 C |

[a]Ten gram of wheat seed was coated with 4 ml of a 0.5% methylcellulose suspension mixed with cells of the respective strains grown on NBY agar for 48 h at 21–24° C. Initial populations of Bacillus strains were 7.2, 7.4 and 7.4 log CFU/seed for L324-92, L331-92 and P206-92, respectively.
[b]Severity of Rhizoctonia root rot was evaluated on a scale ranging from 0 (= no lesion evident) to 8 (= almost no roots with stunting death seedling); severity of take-all was evaluated on a scale from 0 (= no disease evident) to 8 (= plant dead or nearly so).
[c]For Rhizoctonia root rot, one whole oat kernel colonized with *R. solani* AG8 was added to Thatuna silt loam.
[d]Means with the same letter in the same column within the same experiment are not significantly different at P = 0.05 according to Fisher's protected LSD. Treatment means were analyzed using data pooled from raw and steamed soils because of no interaction between soil and seed treatment.
[e]For take-all, soil was infested with 1% of oat-kernel inoculum of *G. g. tritici*.

4. Effect of Bacillus spp. on yield in the field

Strain L324-92 increased the yield of wheat sown on wheat and barley stubble by 22.5% and 24.8%, respectively, as compared with the control. Strain P206-92 had no effect (Table 2). Strain L324-92 also increased seedling emergence and plant height, and decreased the number of lesions caused by *R. solani* AG8 (data not shown). The results show that strain L324-92 applied on the seeds of the spring wheat produced yield increases equal to those produced by fumigation of the soil with methyl bromide, which controls all three root diseases.

TABLE 2

Effect of Bacillus spp. on yield of no-till spring wheat (cv. Penawawa) at Dusty, WA

| Treatment | Yield (ton/ha) |
|---|---|
| Wheat on spring wheat stubble (SWS)[1] | |
| None | 2.68 B[2] |
| Methylcellulose (MC)[3] | 2.63 B |
| Fumigated[4] | 3.70 A |
| L324-92 | 3.28 A |
| Wheat on spring barley stubble (SBS)[1] | |
| None | 2.54 b |
| Fumigated | 3.27 a |
| L324-92 | 3.21 a |
| P206-92 | 2.43 b |

[1]Randomized complete block design with 4 replications for SWS and 5 replications for SBS
[2]Means with same letter in the same experiment are not significantly different at P = 0.05 by Fisher's protected LSD.
[3]Methylcellulose was used to adhere bacteria to the seed.
[4]Soil was fumigated with methyl bromide and used as a "pathogen free" control.

Additional fields tests assessing the effect of Bacillus spp. on disease control of spring wheat were carried out. One example of these results is presented in Table 3 from an experiment carried out in the field on the Washington State University Plant Pathology farm near Pullman. In this experiment, the soil had been fallowed for 1 year, which greatly reduces the level of natural inoculum available for take-all and Rhizoctonia root rot but does not significantly reduce the amount of natural inoculum available for Pythium root rot. The soil was therefore naturally infested with Pythium spores but not inoculum of the fungi responsible for take-all or Rhizoctonia root rot. Inoculum of *R. solani* AG8 was added to the seed furrow at the time of planting spring wheat as sterile oat grains colonized by *R. solani* AG8. No inoculum was added to produce take-all. The results show that strain L324 has activity against both Pythium and Rhizoctonia root rot.

TABLE 3

Effect of seed treatment with Bacillus spp. on Pythium damage (measured as seedling emergence in response to natural infestations of Pythium) and Rhizdctonia root rot (number of infected roots in response to introduced inoculum of *R. solani* AG8) of a spring wheat in a field trial.

| Treatment | Emergence[a] | Rhizoctonia root rot[b] |
|---|---|---|
| Nontreated | 63 C[c] | 2.51 AB |
| Methylcellulose[d] | 75 AB | 3.13 A |
| L324-92[e] | 80 A | 1.63 D |
| L331-92[f] | 65 BC | 1.90 BCD |
| P206-92[g] | 64 BC | 2.29 BC |

[a]Emergence was estimated on the basis of visual assessment of stand establishment scored to the nearest 10%, independently by three people. At the beginning of the assessment, a plot with high density was given a rating of 90%, thereafter other plots were scored with the range of 0–100%.
[b]Rhizoctonia root rot was assessed by counting the number of diseased roots with typical brown lesions and tapered root tips fot a whole root system. Fifteen plants were sampled for each plot with five replicates at the flowering stage.
[c]Means with the same letter in the same column within the same experiment are not significantly different at P = 0.05 according to Fisher's protected LSD.
[d]Seed treated with 1.5% methylcellulose.
[e]Seed treated with Bacillus sp. L324-92 at a dose of 6.30 log CFU/seed.

TABLE 3-continued

Effect of seed treatment with Bacillus spp. on Pythium damage (measured as seedling emergence in response to natural infestations of Pythium) and Rhizoctonia root rot (number of infected roots in response to introduced inoculum of *R. solani* AG8) of a spring wheat in a field trial.

| Treatment | Emergence[a] | Rhizoctonia root rot[b] |
|---|---|---|

[f]Seed treated with cells of *B. subtilis* L331-92 at a dose of 6.50 log CFU/seed.
[g]Seed treated with cells of *B. subtilis* P206-92 at a dose of 6.65 log CFU/seed.

EXAMPLE 2

This example describes the morphological, physiological, and biochemical characteristics of Bacillus strain L324-92.

Bacillus strain L324-92 was examined for Gram reaction, oxygen requirement, spore formation, and catalase reaction. Oxygen requirement of each strain was tested in a jar with an anaerobic atmosphere (BBL GasPak Plus, Becton Dickinson Co., Md.). Endospore formation was tested on NBY amended with 0.003% (w/v) manganese sulfate. Bacterial cultures were spread on the medium, incubated at 25° C. for 3 days, and the cells were then observed for endospore formation under a phase-contrast microscope. Bacillus strain L324-92 also was evaluated using the API 50 CHB system (SA Montalieu, Vericieu, France). Strain L324-92 was sent to both Microbial ID. Inc. (Newark, Del.) and American Type Culture Collection (ATCC; Rockville, Md.) for identification.

The results showed that strain L324-92 is a straight rod-shaped, strictly aerobic, catalase positive, Gram-variable, endospore-forming bacterium. After 5 days of incubation on ¹⁄₁₀ TSA at 27° C., the colonies of L324-92 remained milky-white. L324-92 could not be identified using the API CHB 50 system. Strain L324-92 did not match with any known Bacillus spp. based on whole cell fatty acid analysis conducted by the Microbial ID. Inc, but was closest to *B. maroccanus*. On the basis of standard biochemical and physiological tests conducted by the American Type Culture Collection, L324-92 did not match with any known species, but was closest to *B. badius*. L324-92 differed from *B. badius* in that it was positive for citrate utilization, esculin decomposition, and nitrate reduction, and it grew maximally at 40° C. compared with 50° C. for *V. badius*. The results presented in Table 4 show the morphological, physiological, and biochemical characteristics of Bacillus strain L324-92. These characteristics do not match any known Bacillus species.

TABLE 4

Cellular Morphology: The motile cells are generally found in chains, with one endospore formed in the central or subterminal region. The cells are uniformly stained Gram negative or Gram variable.
Colonial Morphology: The colonies are opaque with convex elevation, a mucoid, glistening smooth surface, and an entire margin with some dull, translucent spreading occurring. The size and shape of the colonies may vary greatly with age, however, all colony types were able to revert to the predominant colony type.

Characterization Tests:

| | | | |
|---|---|---|---|
| Rods | + | Colony translucent | + |
| Rods straight | + | Colony transparent | − |
| Rods curved | − | Colony opaque | + |
| Cells single | + | Colony entire | + |
| Cells chained | + | Colony erose | + |
| Ends tapered | − | Colony rhizoid | − |
| Ends rounded | + | Colony irregular | − |

TABLE 4-continued

Cellular Morphology: The motile cells are generally found in chains, with one endospore formed in the central or subterminal region. The cells are uniformly stained Gram negative or Gram variable.
Colonial Morphology: The colonies are opaque with convex elevation, a mucoid, glistening smooth surface, and an entire margin with some dull, translucent spreading occurring. The size and shape of the colonies may vary greatly with age, however, all colony types were able to revert to the predominant colony type.

| | | | |
|---|---|---|---|
| Ends squared | − | Colony lobate | − |
| Endospore formed | + | Colony low convex | + |
| Sporang swollen | − | Colony high convex | − |
| One spore/cell | + | Colony convoluted | − |
| Spore round | − | Colony flat | − |
| Spore cylindrical | + | Colony raised | − |
| Spore oval | + | Colony moves as unit | − |
| Spore central | + | Colony disassociates | − |
| Spore terminal | − | Colony glistening | + |
| Spore subterminal | + | Colony dull | + |
| Gram stained | + | Colony dry | − |
| Gram positive | − | Colony smooth | + |
| Gram negative | + | Colony rough | − |
| Gram variable | − | Sol. brown pigment | +* |
| Sol. black pigment | − | Hippurate hydrol. | + |

*Soluble and insoluble pigment formed on starch and tyrosine agars.

Characterization Data (cont.)

| | | | |
|---|---|---|---|
| Sol. yellow pigment | − | Starch hydrolyzed | −* |
| Insol. brown pigment | +* | Starch hydrol. weak | − |
| Thsol. black pigment | − | Gelatin liquified | W |
| Insol. yellow pigment | − | Casein hydrolyzed | + |
| Insol. orange pigment | − | Meth. blue reduced | + |
| Insol. red pigment | − | Meth. blue reoxid. | − |
| Cells motile | + | Nitrate reduced | + |
| mofile, flagella | + | $NO_3$ reduced to $NO_2$ | + |
| Growth at 15° C. | + | VP (5198) positive | − |
| Growth at 20° C. | + | VP (5198 fil) pos. | − |
| Growth at 25° C. | + | VP (5331) positive | − |
| Growth at 30° C. | + | $H_2O_2$ decomposed | + |
| Growth at 37° C. | + | Indole | − |
| Growth at 45° C. | W | Tyrosine decomposed | −St* |
| Growth at 50° C. | − | Dihydroxyacetone | − |
| Growth in 5% NaCl | + | Litmus milk acid | − |
| Growth in 7% NaCl | W | Litmus milk coagulated | − |
| Growth in 10% NaCl | − | Litmus milk alkaline | + |
| Acid from L-arabinose | − | Litmus milk peptonized | − |
| Acid delayed > 14 days | − | Litmus milk reduced | + |
| Gas from L-arabinose | − | Growth at pH 6.0 | + |
| Acid from D-xylose | − | pH VP 5198 6.0 or less | − |
| Acid delayed > 14 days | − | pH VP 5198 7.0 ± 0.5 | + |
| Gas from D-xylose | − | pH VP 5198 8.0 or more | − |
| Acid from D-glucose | − | Aerobe | + |
| Acid delayed > 14 days | − | Facultative | − |
| Gas from D-glucose | − | Microaerophile | − |
| Acid from lactose | − | Anaerobe | − |
| Acid delayed > 14 days | − | Growth in 0.02% azide | − |
| Gas from lactose | − | Gas from sealed nitrate | − |
| Acid from sucrose | − | Growth in sealed glucose | − |
| Acid delayed > 14 days | − | Lecithinase | − |
| Gas from sucrose | − | Oxidase | + |
| Acid from D-mannitol | − | Esculin | + |
| Acid delayed > 14 days | − | Tween 80 | + |
| Gas from D-mannitol | − | Urease | + |
| Propionate util. | W | Phenylalanine | − |
| Citrate util. | + | | |

\* = Soluble and insoluble pigment formed
W = weak
St = strong

EXAMPLE 3

This example shows the spectrum of in vitro inhibitory activity of Bacillus sp. L324-92 against fungal root pathogens.

The results presented in Table 5 show the spectrum of inhibitory activity of strain L324-92 to other species and subspecies of Rhizoctonia and Pythium in addition to strains of the pathogens responsible for take-all, Rhizoctonia root rot, and Pythium root rot. These results show that strain L324-90 was inhibitory to all 36 of 36 isolates of *G. g.* var. *tritici* tested, all 46 of 46 isolates of Rhizoctonia tested, representing eight anastomosis groups of *R. solani* and three anastomosis groups of *R. oryzae,* and all 13 of 13 isolates of Pythium spp. tested, representing twelve species of Pythium.

TABLE 5

Spectrum of in vitro inhibitory activity of
Bacillus sp. L324-92 against fungal root pathogens[a]

| Genus | Species | Subgroup | A/B[b] | C/D[c] (mm/mm) |
|---|---|---|---|---|
| Gaeumannomyces | gruminis | tritici | 36/36 | 19/31 |
| Rhizoctonia | solani | AG1 | 2/2 | 18/40 |
| | | AG2-1 | 3/3 | 19/38 |
| | | AG2-2 | 3/3 | 15/32 |
| | | AG3 | 3/3 | 16/29 |
| | | AG4 | 12/12 | 16/31 |
| | | AG5 | 3/3 | 17/37 |
| | | AG6 | 3/3 | 16/30 |
| | | AG8 | 12/12 | 15/26 |
| | oryzae | AG-D | 1/1 | 18/33 |
| | | AG-E | 1/1 | 18/32 |
| | | WACO | 3/3 | 18/25 |
| Pythium | irregulare | | 1/1 | 13/40 |
| | ultimum | ultimum | 1/1 | 15/40 |
| | ultimum | sporanghferum | 2/2 | 13/40 |
| | aristosporum | | 1/1 | 12/40 |
| | gramineum | | 1/1 | 10/40 |
| | heterothallicum | | 1/1 | 14/40 |
| | intermedium | | 1/1 | 20/40 |
| | macrosperma | | 1/1 | 15/40 |
| | rostratum | | 1/1 | 17/40 |
| | sylvaticum | | 1/1 | 35/40 |
| | torulosum | | 1/1 | 15/50 |
| | volvotum | | 1/1 | 7/15 |

[a] A 10 μl aliquot of strain L324-92 was spotted at the opposite edges of 1/5PDA plates, and the plates were incubated at 15° C. After 2 days, one disc (8 mm diameter) of each fungus was placed in the center, and then the plates were incubated further at 15° C. for 1 week.
[b] A = number of fungal isolates inhibited by Bacillus sp. L324-92; B = number of isolates tested.
[c] The values are pooled mean of all isolates tested. Mean for each isolate was estimated with 10 measurements (= five plates). C = radius (mm) of the fungal colony in the direction of the bacterial colonies; D = radius of the fungal colony in the direction with no bacteriai colonies.

EXAMPLE 4

The following example presents data comparing Bacillus sp. L324-92, and *B. subtilis* A13, a known biocontrol strain with inhibitory activity.

Any strain intended for biological control of root diseases of no-till cereals must be adapted to the cold soils typical of fields in temperate areas in the late fall or early spring with soils insulated from the sun's rays by surface residues. The growth of Bacillus strains L324-92 and *B. subtilis* A13 were therefore compared at 10, 15 and 20° C. in nutrient-broth-yeast (NBY) broth. Growth of each bacterium was measured spectrophotometrically at 600 nm ($A_{600}$) every 12 h. Fifty microliters of each strain, grown overnight in 5 ml of NBY broth ($A_{600}$=0.1) at 21°–24° C., were transferred individually into 50 ml of NBY broth in 250-ml Erlenmeyer flasks and placed on a rotary shaker at 150 rpm at each temperature. Each treatment was replicated three times, and the experiment was repeated.

Figure 3A:
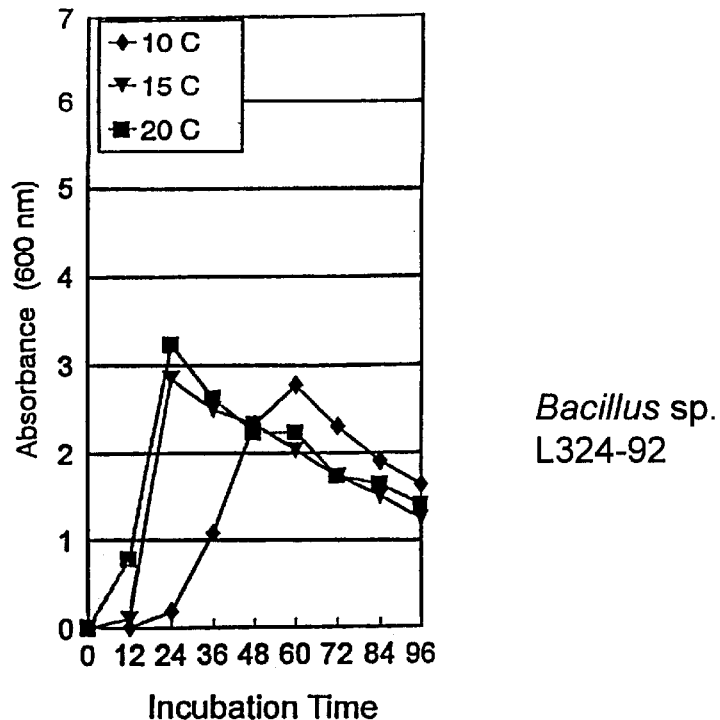
Figure 3B:
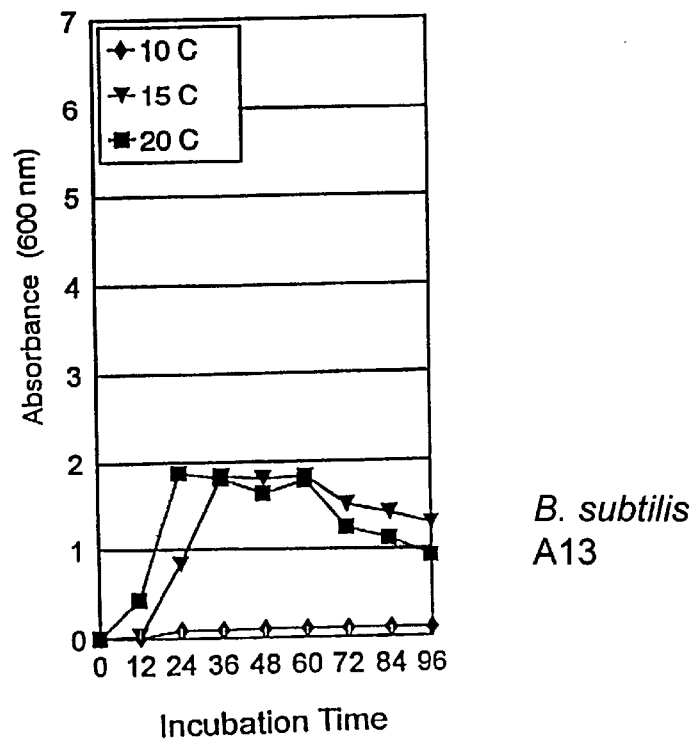

The results of growth by L324-90 at different temperatures are shown in FIG. 3. The vertical bars represent standard deviations with three replicates. These results show that Bacillus sp. L324-92 grew better than *B. subtilis* A13 at 15 and 20° C. and only L324-92 (not A13) grew at 10° C. In another test, L324-92 grew at temperatures as low as 4° C., with doubling time of 55.2 h between 7 and 14 days after inoculation in 25 ml of NBY broth. Thus, strain L324-92 not only is taxonomically very different from A13, it also differs in its ability to grow at 4° C., compared with A13, which does not grow at temperatures below 10° C. No other strain of Bacillus shown to have potential for protection of plants against soilborne plant pathogens has been reported to grow at temperatures down to 4° C. Strain L324-92 can grow at temperatures ranging from 4 to 40° C.

EXAMPLE 5

This following example shows comparison data of seedling vigor using treatments of microorganisms alone, fungicide alone, and combination of microorganisms and fungicide. This test was designed to evaluate the ability of a seed treatment product to simultaneously control the three root diseases as described in Embodiment 1, above.

The experiment was conducted with cores of undisturbed field soil from a no-till wheat field wherein the soil contained the three root pathogens. Each core was 6 inches in diameter and 6 inches deep and was placed in 6-inch diameter pots on a greenhouse bench. Immediately after the cores were brought into the greenhouse, they were watered to the equivalent of field capacity in order to promote the germination of volunteer seed deposited at harvest. Once the volunteer germinated it was killed with glyphosate. Ten seeds were sown in each pot at a depth of about 1 cm, and plants were grown for 4 weeks. Pots were watered each week or as needed with a Hoagland's solution (macroelements only).

Each treatment consisted of six replicate pots. The treatments consisted of no treatment (control), Bacillus sp. L324-92, *Pseudomonas fluorescens* Q69c-80, difenoconazole (DIVIDEND), L324-92 plus difenoconazole, and Q69c-80 plus difenoconazole. In both individual and combination treatments, L324-92 and Q69c-80 were applied, respectively, at a rate of 5.7 and 8.0 log CFU/seed. DIVIDEND was applied at a rate of 0.5 oz/100 lb of seed. Effective seed treatment products were identified on the basis of comparisons of the growth of treated plants to the nontreated control plants. Parameters measured included emergence and plant height.

Figure 4:
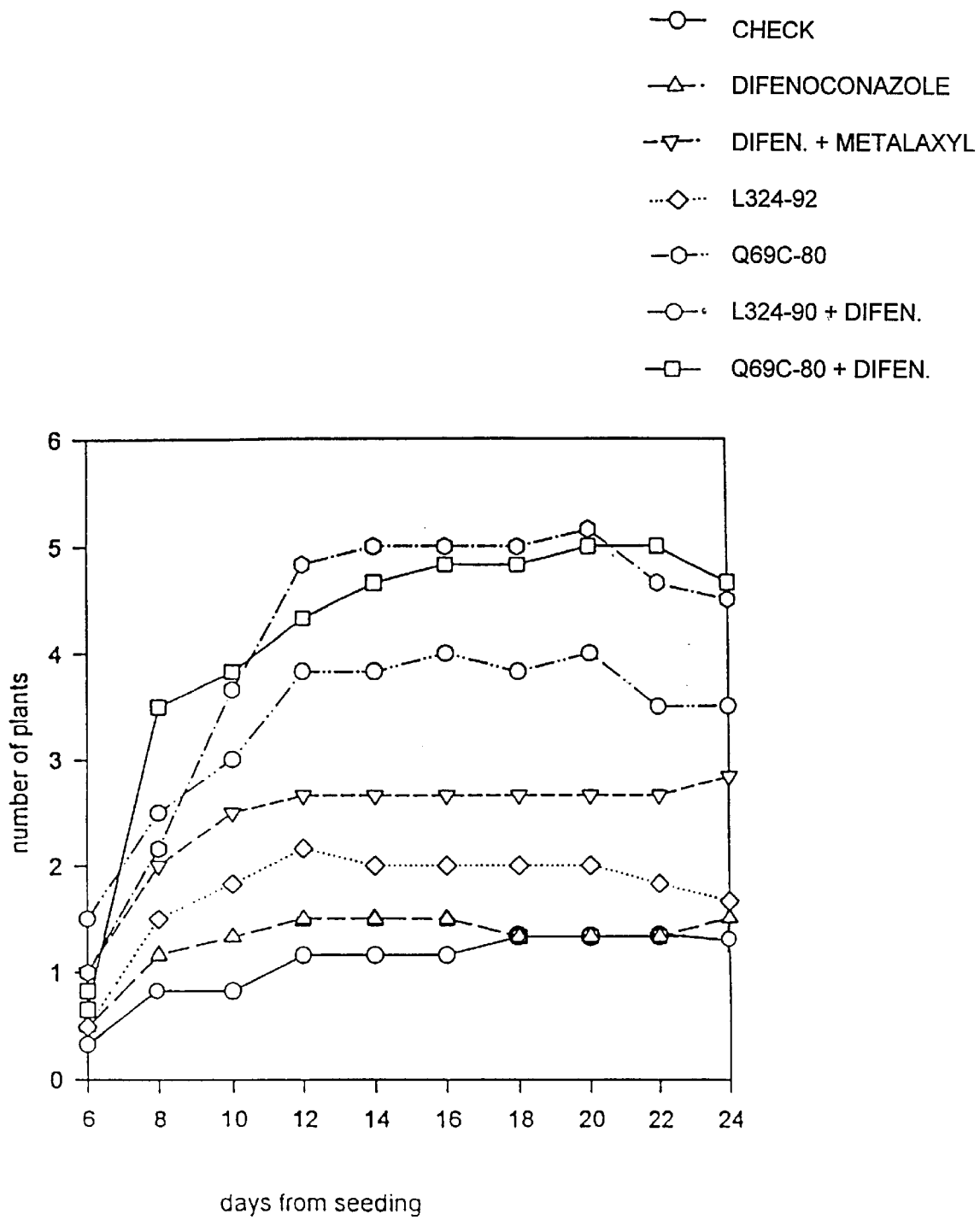

Table 6 shows the number of plants that had emerged and the height of seedlings after four weeks of growth when the experiment was terminated. Each value is the average from six pots. Emerged plant number is the average number of plants that emerged per pot. Plant height of each seedling was measured from the soil surface to the tip of the longest leaf. The results show improvement in seedling vigor by all of the treatments with L324-92 plus difenoconazole and Q69c-80 plus difenoconazole providing the greatest increases in plant height. As compared to the control, L324-92 plus difenoconazole and Q69c-80 plus difenoconazole increased plant height 91% and 99%, respectively. The rate of seedling emergence was also studied in this soil core experiment (FIG. 4). Data for seeds treated with difenoconazole (DIVIDEND) plus metalaxyl (APRON) are also included in FIG. 4. As can be seed in the figure, Bacillus sp.

L324-92 plus difenoconazole increased the amount and rate of emergence of seedlings as compared to the nontreated control, L324-92 alone or difenoconazole alone. It should be noted that in FIG. 4, the decline in the number of plants in some of the treatments at the end of the experiment is due to the fact that some plants emerged and were counted and then rapidly died and then were no longer counted.

TABLE 6

| Treatment | Emerged plants No. | Plant Height cm. |
|---|---|---|
| Check | 7 | 9.2 |
| L324-92 | 13 | 15.8 |
| Q69c-80 | 28 | 16.5 |
| Difenoconazole | 9 | 15.7 |
| L324-92 + Difen. | 24 | 17.6 |
| Q69c-80 + Difen. | 28 | 18.3 |

EXAMPLE 6

This example describes the composition of fungicide and microorganism for field control of the combination of pathogens that cause the three kinds of root disease.

The treatments consisted of non-treated winter wheat (control), Bacillus sp. L324-92 plus difenoconazole, *Pseudomonas fluorescens* Q69c-80, difenoconazole (DIVIDEND), L324-92 plus difenoconazole (Bonanza 1), and Q69c-80 plus difenoconazole (Bonanza 2). In both individual and combination treatments, L324-92 and Q69c-80 were applied, respectively, at a rate of 5.7 and 8.0 log CFU/wheat seed. DIVIDEND was applied at a rate of 0.5 oz/100 lb of seed. Fumigation of the soil with methyl bromide at 50 g/m$^2$ is included as a healthy control because it eliminates all three pathogens from the soil. Both seeds and fertilizer were placed directly as a "one pass" operation directly into standing stubble (no-till) of spring wheat. The drill was equipped with fertilizer shanks to both loosen the soil in the seed furrow and to place nitrogen, phosphate, and sulfur (NPS) 6 to 8 cm beneath the seed. The winter wheat cv. Madsen was sown at a rate of 90 kg/ha in October 1995 in a field near Almota, Wash. Each treatment replicate consisted of eight rows. Yields were obtained by harvesting the five center rows out of each eight-row plot, leaving one border row on one side and two border rows on the other side of each harvested replicate.

Results. The two seed-treatment products, referred to as Bonanza 1 and Bonanza 2, out performed difenoconazole and L324-92 and Q69c-80 used individually. Bonanza 1 increased yield 21%, 20% and 20% as compared to the nontreated check, difenoconazole, and L324-92, respectively. Bonanza 2 increased yield 15%, 15% and 21% as compared to the nontreated check, difenoconazole, and Q69c-80, respectively. Fumigation of the soil with methyl bromide resulted in the greatest yield increase, 36% increase compared to the nontreated check, because all three pathogens were eliminated.

TABLE 7

Yields of Madsen winter wheat planted directly (no-till) into standing stubble of spring wheat (Field A).

| Treatment | Yield (bu/A) |
|---|---|
| Fumigated soil | 85.8 a[1] |
| Natural soil | |
| Check | 62.9 c |
| Difenoconazole | 63.4 c |
| Q69c-80 | 60.2 c |
| L324-92 | 63.7 c |
| L324-92 + Difenoconazole | 76.2 b |
| Q69c-80 + Difenoconazole | 72.6 b |

[1]Values not followed by the same letter are significantly different at P = 0.1.

It is understood that the foregoing detailed description is given merely by way of illustration and that modification and variations may be made within without departing from the spirit and scope of the invention.

What is claimed is:

1. Bacillus strain NRRL B-21525.

2. A biocontrol composition useful for field control of the root diseases caused by *Gaeumannomyces graminis*, Rhizoctonia, and Pythium, which comprises a chemical fungicide and said Bacillus strain of claim 1.

3. A The biocontrol composition of claim 2, wherein said chemical fungicide is difenoconazole.

4. A product comprising a seed of a cereal or legume grain crop coated with said Bacillus strain of claim 1, the concentration of said strain being about $10^4$ to $10^8$ colony forming units per seed.

5. The product of claim 4 which further includes a chemical fungicide.

6. A method of controlling the root diseases caused by *Gaeumannomyces graminis*, Rhizoctonia, and Pythium in crops susceptible to said root diseases, which comprises treating seed of said crop with a composition comprising an effective amount of said Bacillus strain of claim 1.

7. The method of claim 6 wherein said composition further includes an effective amount of a chemical fungicide.

8. The method of claim 7 wherein said chemical fungicide is difenoconazole.

* * * * *